United States Patent
Zhou et al.

(12) 
(10) Patent No.: US 6,472,572 B1
(45) Date of Patent: Oct. 29, 2002

(54) INTEGRATED PROCESS FOR SYNTHESIZING ALCOHOLS AND ETHERS FROM ALKANES

(75) Inventors: Xiao Ping Zhou, Goleta, CA (US); Ivan Marc Lorkovic, Santa Barbara, CA (US); Galen D. Stucky, Goleta, CA (US); Peter C. Ford, Santa Barbara, CA (US); Jeffrey H. Sherman, The Woodlands, TX (US); Philip Grosso, Auburn, CA (US)

(73) Assignees: GRT, Inc., The Woodlands, TX (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 09/886,078

(22) Filed: Jun. 20, 2001

(51) Int. Cl.$^7$ .......................... C07C 27/00; C07C 41/00; C07C 27/10
(52) U.S. Cl. ...................... 568/893; 568/671; 568/891; 568/910
(58) Field of Search ................................. 568/910, 671, 568/891, 893

(56) References Cited

U.S. PATENT DOCUMENTS

| | | |
|---|---|---|
| 3,172,915 A | 3/1965 | Borkowski et al. |
| 3,310,380 A | 3/1967 | Lester |
| 5,243,098 A | 9/1993 | Miller et al. ................. 568/893 |
| 5,334,777 A | 8/1994 | Miller et al. ................. 568/859 |
| 5,998,679 A | 12/1999 | Miller ......................... 568/859 |

FOREIGN PATENT DOCUMENTS

WO     WO 00/07718     2/2000

OTHER PUBLICATIONS

Selective Monohalogenation of Methane over Supported Acid or Platinum Metal Catalysts and Hydrolysis of Methyl Halides over y–Alumina–Supported Metal Oxide/Hydroxide Catalysts. A Feasible Path for the Oxidative Conversion of Methane into Methyl Alcohol/Dimethyl Ether; George B. Olah, et al.; Contribution from the Donald P. and Katherine B. Loker Hydrocarbon Research Institute and Department of Chemistry, University of Southern California, Los Angeles, CA, received Apr. 22, 1985.

Ionic Bromination of Ethane and Other Alkanes (Cycloalkanes) with Bromine Catalyzed by the Polyhalomethane 2A 1Br3 Aprotic Organic Superacids under Mild Conditions; Irena S. Akhren, et al.; Tetrahedron Letters, vol. 36, No. 51, pp. 9365–9368, 1995.

Selective bromination of alkanes and arylalkanes with CBr4; Vladimir V. Smirnov, et al., Mendeleev Communications Electronic Version, Issue 5, 2000 (pp. 167–206).

*Primary Examiner*—Samuel Barts
*Assistant Examiner*—Elvis O. Price
(74) *Attorney, Agent, or Firm*—Michael A. O'Neil, P.C.

(57) ABSTRACT

Methanol and/or dimethyl ether are manufactured from methane by mixing methane and bromine in a reactor to form methyl bromide and hydrogen bromide. The methyl bromide only or the methyl bromide and the hydrogen bromide are directed into contact with metal oxide to form methanol and/or dimethyl ether and a metal bromide. The metal bromide is oxidized to form original metal oxide catalyst and bromine, both of which are recycled.

32 Claims, 3 Drawing Sheets

INTEGRATED PROCESS FOR SYNTHESIZING ALCOHOLS AND ETHERS FROM ALKANES

TECHNICAL FIELD

This invention relates generally to the synthesis of alcohols and ethers from alkanes, and more particularly to a method of and apparatus for manufacturing methanol and dimethyl ether from methane.

BACKGROUND OF THE INVENTION

Methane has previously been converted to methanol by the halogenation of methane followed by hydrolysis of the methyl halide to form methanol. For example, gaseous chlorine has been used to chlorinate methane to form chlorinated methane, principally methyl chloride, together with other chlorides, i.e., dichloromethane, trichloromethane and carbon tetrachloride. Alternatively, methane has been subjected to oxychlorination with oxygen and hydrochloric acid to form the foregoing compounds. The chlorinated methanes produced are hydrolyzed in the vapor phase to produce methanol, formaldehyde, formic acid and by-products, including carbon dioxide and hydrochloric acid, depending on the chlorination selectivity. Hydrochloric acid is produced or used in the halogenation of methane by either method and must be recovered, dehydrated by azeotropic distillation and recycled. Corrosion and other problems involved with the handling of chlorine and hydrochloric acid are substantial.

U.S. Pat. No. 3,172,915 awarded to Borkowski, et al. is directed to a process for converting methane to methanol. Borkowski discloses the chlorination of methane using ferric chloride at high temperatures to produce chloromethanes and hydrogen chloride. The process requires temperatures in the range of 220–800° C., more preferably 250–450° C., and long residence times, e.g., more than one hour. Further, the process is hindered by the production of a mixture of chlorination products, e.g., chloromethane, dichloromethane, trichloromethane and carbon tetrachloride, which must be separated before hydrolysis to methanol. Other disadvantages result from the energy required to dry the ferric chloride and from the corrosion and handling problems inherent with hydrochloric acid.

U.S. Pat. No. 5,243,098 awarded to Miller discloses another method for converting methane to methanol. In the Miller process the reaction of methane with cupric chloride produces chloromethane and hydrochloric acid. These intermediates are then reacted with steam and a catalyst containing magnesium oxide to produce methanol and magnesium chloride. Magnesium oxide is regenerated by treatment of the magnesium chloride by-product with air or oxygen. Cupric chloride is regenerated by treatment of the cuprous chloride by-product with air and hydrochloric acid. While these reactions proceed at favorable rates, attrition of the solid reactants, i.e., cupric and magnesium oxide, is significant. Special filters and processes were required to recover and regenerate these reactants in the required particle size. Miller also suggests cupric bromide and magnesium zeolite as alternative reactants. Because of the attrition of the reactants, difficulties associated with the handling of solids, and the special filters and processes required to regenerate the reactants, the Miller process has proved unsatisfactory. U.S. Pat. No. 5,334,777, also awarded to Miller, discloses a nearly identical process for converting ethane to ethylene glycol.

U.S. Pat. No. 5,998,679 awarded to Jorge Miller, discloses a process for converting alkanes and alkenes to the corresponding lower alkanols and diols. In the methods of the invention, a gaseous halogen (bromine) is produced by decomposing a metal halide in a liquid having a melting point below and a boiling point above the decomposition temperature of the metal halide. The preferred liquid is molten hydrated ferric chloride maintained at a temperature between about 37–280° C. The lower alkane or alkene is halogenated in a gas phase reaction with the halogen. The resulting alkyl halide or alkyl dihalide is contacted with a metal hydroxide, preferably an aqueous solution of ferric hydroxide, to regenerate the metal halide and produce the corresponding lower alkanol or diol. Problems with this process include low monohalogenation selectivity, and corrosiveness of the hydrated ferric halides, which may present a containment problem if the process is run at 280° C., where high pressures of steam are required to maintain ferric halide hydration. Finally, the process produces a great deal of water and HCl or HBr, all of which are difficult to separate on a large scale from the desired product methanol.

Published international patent application WO 00/07718, naming Giuseppe Bellussi, Carlo Perego, and Laura Zanibelli as inventors, discloses a method for directly converting methane and oxygen to methanol over a metal halides/metal oxides catalyst. This is not a catalyst in the true sense of the word, however, because the reaction by halogen transfer of halide from a metal halide (via reaction with methane) to a different metal oxide (giving the metal halide and methanol) occurs downstream. Eventually the halide is leached and the catalyst loses activity. Olah et al. (George A. Olah, et al. *J. Am. Chem. Soc.* 1985, 107, 7097–7105) discloses a method for converting methane to methanol via methyl halides ($CH_3Br$ and $CH_3Cl$), which are then hydrolyzed to prepare methanol. In the process, $CH_3Br$ and $CH_3Cl$ are hydrolyzed over catalysts with excess steam generating a methanol, water, and HCl or HBr mixture. The separation of methanol (about 2% by mole) from HCl or HBr and water on an industry scale (2000 tons per day) requires an enormous amount of energy and generates a great deal of aqueous HCl and HBr waste. Aqueous HCl and HBr are very corrosive as well.

SUMMARY OF THE INVENTION

The present invention uses bromine or bromine containing compounds as intermediates to convert alkanes such as methane, ethane, propane, butane, and isobutane to ethers and alcohols by reaction with oxygen (or air) in a process. While the process can be used to convert a variety of alkanes, including methane, ethane, propane, butane, and isobutane, to their respective ethers and alcohols, the conversion of methane to methanol and dimethyl ether is illustrative.

Methane reacts with bromine over a catalyst to form $CH_3Br$ and HBr. $CH_3Br$ and HBr react with a metal oxide to form a variable mixture of dimethyl ether (DME), water, and methanol and the metal bromide. The metal oxides and molecular bromine are regenerated by reaction of metal bromide with air and/or oxygen. The regenerated bromine is recycled to react with methane while the regenerated metal oxide is used to convert more methyl bromide and HBr to methanol and DME, completing the reaction cycle.

The process can be easily carried out in a riser reactor. Compared to the current industrial two step process, in which methane and steam are first converted to CO and $H_2$ at 800° C. followed by conversion to methanol over a Zn—Cu—Al—C catalyst at approximately 70–150 atmospheres, the process of the present invention operates at roughly atmospheric pressure and relatively low temperatures, thereby providing a safe and efficient process for methanol production.

The present invention operates with solid/gas mixtures at atmospheric pressure. In the process, hydrogen halide is gaseous, and not as corrosive as when aqueous at high temperature. The reaction of $Br_2$ with an alkane, such as methane, ethane or propane, can reach more than 90% selectivity (at high conversion) to alkane-monobromide. The main side products, alkane dibromides such as $CH_2Br_2$, can be converted back to the monobromides by reaction with an alkane over another catalyst. Very few by-products are produced. During operation, most of the Br atoms are trapped in the solid state, making the system less corrosive. Another advantage is that in the process, DME and alcohol ($CH_3OH$) are not produced as a mixture with excess water. By controlling reaction conditions, almost pure DME and/or methanol is obtained directly so that it is not necessary to separate $CH_3OH$ from water. The process is water free and does not generate wastewater, unlike the processes of the prior arts. Finally, in the present process, methane and oxygen do not come into direct contact, resulting in improved safety.

BRIEF DESCRIPTION OF THE DRAWINGS

A more complete understanding of the present invention may be had by reference to the following Detailed Description when taken in connection with the accompanying Drawings, wherein.

DETAILED DESCRIPTION

Alkanes (methane, ethane, propane, butane, and isobutane) react with molecular bromine over a catalyst composed of all possible metal compounds and their mixtures to form alkylbromides. For $CH_4$ (although the process may be applied to higher alkanes as well), the process of the present invention can convert more than 50% $CH_4$ to $CH_3Br$ and HBr, with selectivity higher than 90%. Most of the by-product is $CH_2Br_2$ (+2 HBr), which can be catalytically reconverted to $CH_3Br$ by reacting $CH_2Br_2$ with $CH_4$.

Figure 1:
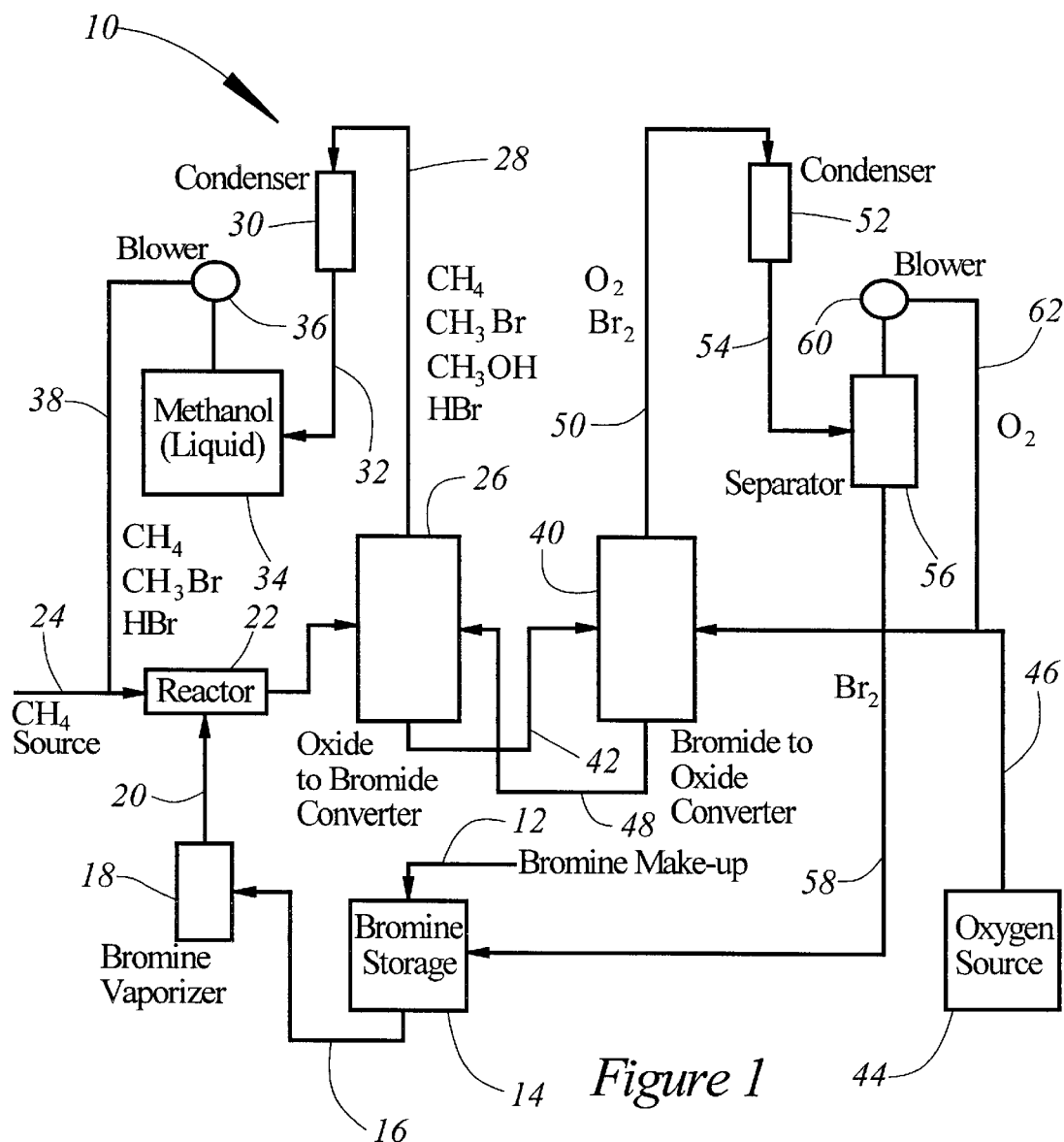
FIG. 1 is a schematic illustration of a method of and apparatus for synthesizing alcohols and/or ethers from alkanes comprising a first embodiment of the invention.

Referring to the Drawings, and particularly to FIG. 1, a method of and apparatus for synthesizing alcohols and ethers from alkanes using bromine 10 is schematically illustrated. In the operation of the method and apparatus 10, bromine is received from a suitable source through a line 12 and is received in a bromine storage container 14. For example, bromine is easily manufactured from bromide, which is readily available from sea water.

As is well known, bromine is a liquid at room temperature. Liquid bromine from the storage container 14 is directed through a line 16 to a bromine vaporizer 18 wherein the bromine is converted from the liquid phase to the gas phase. From the vaporizer 18 the gaseous bromine is directed through a line 20 to a reactor 22.

Methane from a suitable source is directed to the reactor 22 through a line 24. Within the reactor 22 the methane and the gaseous bromine are mixed together. Within the reactor 22, the temperature of the mixture is raised to between about 20° C. and about 400° C., thereby converting the methane and the bromine to methyl bromide ($CH_3Br$) and hydrogen bromide (HBr).

From reactor 22, the $CH_3Br$, the HBr, and any unreacted methane are directed to a converter 26. The converter 26 comprises a solid metal oxide, such as copper oxide (CuO). When it engages the solid metal oxide within the converter 26, the $CH_3Br$ and HBr are converted to methanol ($CH_3OH$) and DME.

Methanol, ether , unreacted methyl bromide, and unreacted methane are recovered from the converter 26 through a line 28 and are directed to a condenser 30. Within the condenser 30, the DME and methanol from the converter 26 are condensed to liquid. Liquid methanol and DME is recovered from the condenser 30 through a line 32 and is stored in a container 34. Unreacted methane, unreacted hydrogen bromide, and methyl bromide are removed from the container 34 by a blower 36 and are returned to the reactor 22 through a line 38 and the line 24.

In addition to producing methanol, the reaction within the converter 26 produces copper bromide ($CuBr_2$). Copper bromide is continuously removed from the converter 26 and is directed to a converter 40 through a line 42. For example, the copper bromide can be removed from the converter 26 by gravity and transported by mechanical or pneumatic conveying systems.

The converter 40 receives oxygen or air from a source 44 through a line 46. Within the converter 40 the oxygen from the source 44 converts the copper bromide to copper oxide. The copper oxide is returned from the converter 40 to the converter 26 through a line 48.

The reaction within the converter 40 also provides bromine ($Br_2$) Bromine and any unreacted oxygen are directed through a line 50 to a condenser 52 wherein the bromine is condensed to liquid. From the condenser 52 the liquid bromine is directed through a line 54 to a separator 56. From the separator 56 the liquid bromine is directed through a line 58 to the bromine storage container 14. A blower 60 is utilized to remove unreacted oxygen from the separator 56. The unreacted oxygen and some uncondensed bromine are directed through a line 62 and the line 46 to the converter 40.

Figure 2:
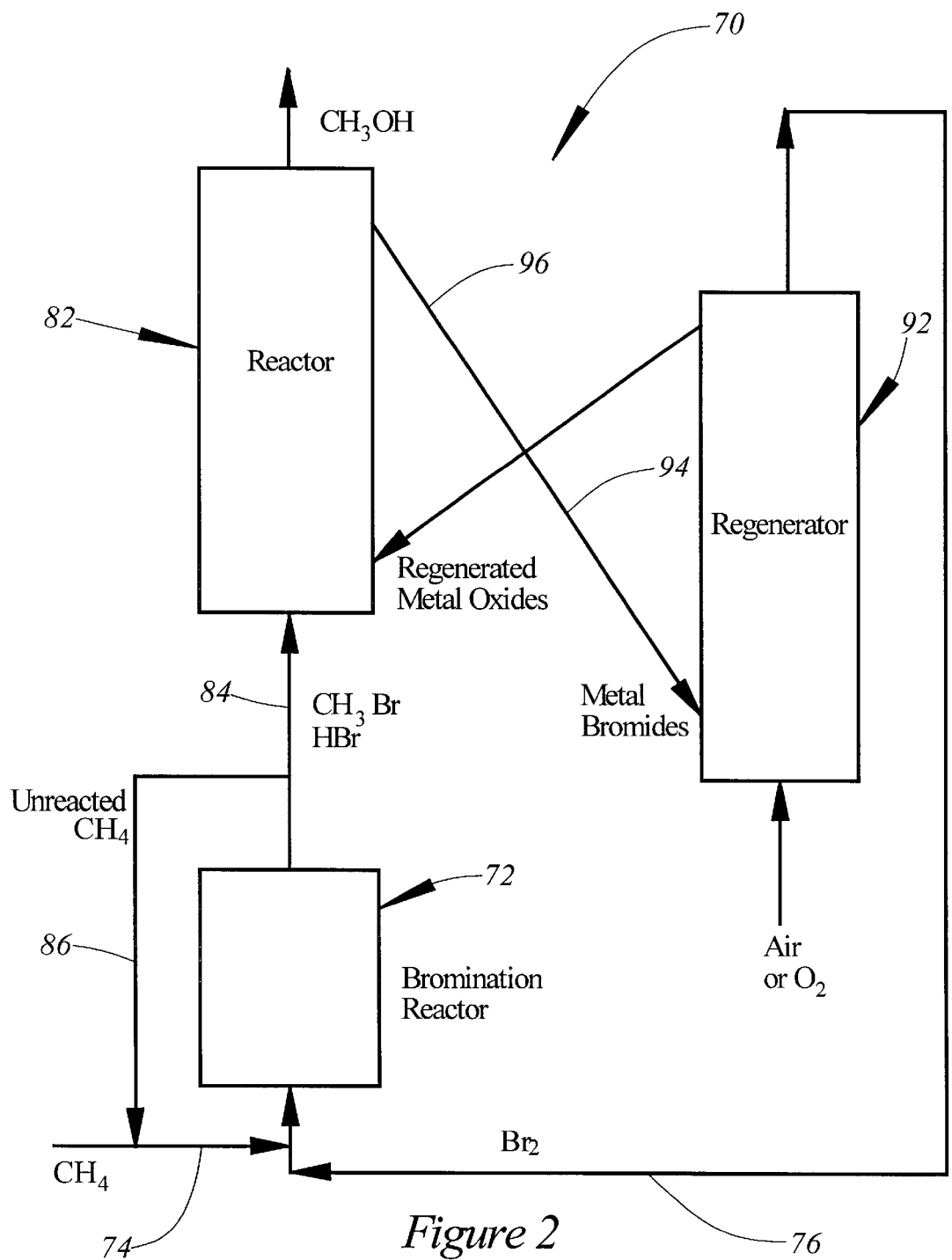
FIG. 2 is a schematic illustration of a method of and apparatus for synthesizing alcohols and/or ethers from alkanes comprising a second embodiment of the invention.

Referring to FIG. 2, there is shown a method of and apparatus for synthesizing alcohols and ethers from alkanes 70 comprising a second embodiment of the invention. Methane and bromine are directed to a first reactor 72 through lines 74 and 76, respectively. Within the first reactor 72, the methane and bromine react to form methyl bromide ($CH_3Br$) and hydrogen bromide (HBr) which are directed to a second reactor 82 through a line 84. Excess methane is returned to the line 74 through a line 86.

$CH_3Br$ and HBr react with a metal oxide ($Mo_x$) in the second reactor 82 yielding DME, methanol and $MBr_{2x}$ ($Mo_x$ and $MBr_{2x}$ comprise all possible metal oxides and the corresponding metal bromides, respectively). The $MBr_{2x}$ is directed to a third reactor 92 as indicated by the arrow 94 and is reacted with $O_2$ to regenerate $Br_2$ and $MO_x$. The $Br_2$, in gaseous form, is sent back to the first reactor through the line 76 to react with the $CH_4$ feed. As indicated by the arrow 96, the $MO_x$ is transferred to the second reactor 82 for further $CH_3Br$ conversion to $CH_3OH$. The overall reaction is thus $CH_4 + ½O_2 > CH_3OH$.

The transfer of $MBr_{2x}$ and $MO_x$ between the second and third reactors 82 and 92 may be achieved using riser reactor technology. The process of the present invention does not require high pressure and temperature to synthesize methanol from methane and oxygen. Compared to the current CO and hydrogenation process (800° C., 70–150 atm), use of the process reduces capital investment cost as well as operating expense while retaining a greater fraction of the original energy value of the original gas stream, which would otherwise be consumed in achieving and maintaining the high pressures and temperatures of the prior art technology. In the process, bromine containing compounds act as mediators to transfer oxygen atoms between metal oxides and alkanes. There is minimal direct contact between alkanes and oxygen, making the process a practical and safe way to synthesize alcohols and ethers compared to prior art processes for the direct conversion of alkanes and oxygen to alcohols. Based on the process, almost 100% alcohol and/or ether selectivity can be reached at more than 20% alkane conversion, and the product ether and/or alcohol, such as methanol does not require energy intensive separation from HBr or water.

Figure 3:
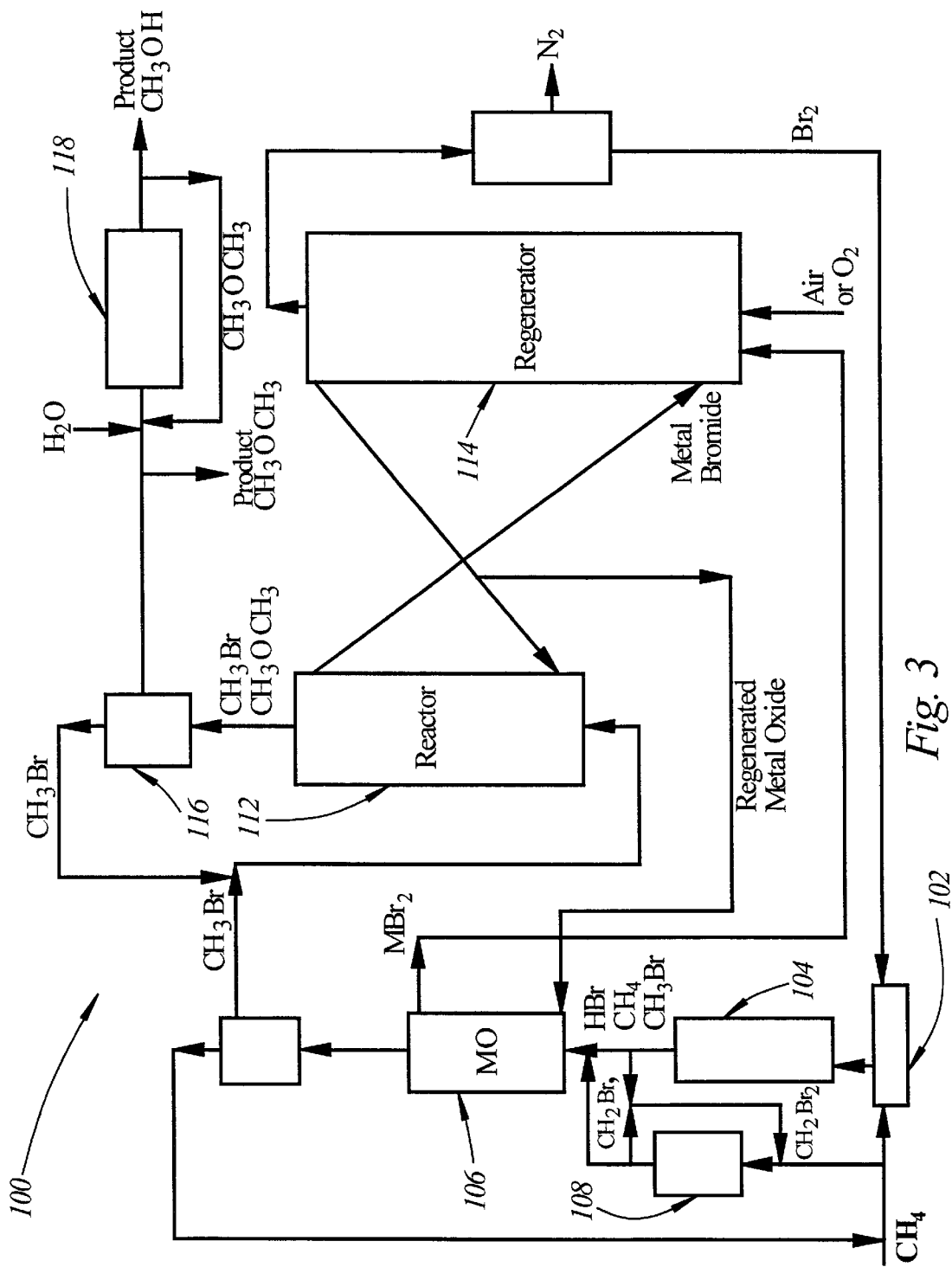
FIG. 3 is a schematic illustration of a method of and apparatus for synthesizing ethers and/or alcohols from alkanes comprising a third embodiment of the invention.

Referring to FIG. 3, there is shown a process for pure ether or pure alcohol synthesis from alkanes 100 comprising a third embodiment of the invention. Methane and bromine are mixed and heated to gas in the heater-vaporizer 102, then the reactant gas mixture is sent to reactor 104. After reaction, a mixture containing methylbromide, hydrogen bromide, and unreacted methane is passed to reactor 106, while by product $CH_2Br_2$ is sent to reactor 108 to react with methane to convert to $CH_3Br$ and then sent to reactor 106. Metal oxide(s) is packed in reactor 106. In reactor 106, the temperature is controlled to only let HBr to react with metal oxide, while $CH_3Br$ cannot react with metal oxide at this temperature. After reaction in reactor 106, there is no remaining HBr. Only methane and $CH_3Br$ are left, which are separated in separator 110. After separation, methane is sent back to reactor 104, while $CH_3Br$ is sent to reactor 112. After reaction in reactor 106, the metal oxide is converted to methal bromide. The metal bromide is sent to reactor 114 to regenerate it back to metal oxide and sent back to reactor 106.

In reactor 112, $CH_3Br$ reacts with metal oxide, which is the same material as that in reactor 106 to generate dimethyl ether (DME). After reaction, a mixture of DME and $CH_3Br$ is obtained. The mixture is separated in separator 116 to DME and $CH_3Br$. The $CH_3BR$ is recycled back to reactor 112, and DME is obtained as a product or sent to separator 116 to react with water to produce methanol. After reaction in reactor 112, the metal oxide is converted to metal bromide, which is sent to reactor 114 to regenerate it back to metal oxide by reacting with air or oxygen. After regeneration, metal oxide is sent back to reactor 112, while bromine is sent to reactor 104. In this process, DME can be produced as the only product, and DME can also be hydrolyzed to methanol.

EXAMPLES

Reaction 1

Example A

A gas stream containing 3 parts methane and 1 part bromine is passed through a heated pyrex tube at 400° C. at a flow of 200 h$^{-1}$. The reaction consumes 100% of the $Br_2$, with the brominated methane distribution being 60% (13.3% yield/pass) $CH_3Br/HBr$, 30% $CH_2Br_2/2HBr$ (6.7%), and 10% $CHBr_3/3HBr$ (2.2%), giving 22% overall conversion of methane per pass. In addition to the brominated methane, one equivalent of HBr is produced for every $Br_2$ molecule consumed.

Example B

A gas stream containing 3 parts methane and 1 part bromine at slightly above atmospheric pressure is passed at 100 h$^{-1}$ through a pyrex tube containing 5 g of activated sulfated $ZrO_2$ (zirconia) at 250° C. 100% of the bromine is consumed, with the brominated methane distribution consisting of 90% (27.3% yield/pass) $CH_3Br/HBr$, and 10% (3.0%) $CH_2Br_2/2HBr$, for an overall methane conversion of 30.3%.

Example C

A gas stream containing 3 parts methane and 1 part bromine at slightly above atmospheric pressure is passed at 100 h$^{-1}$ through a pyrex tube containing 5 Å molecular sieves calcined with 20% by weight $ZrO_2$. The reaction consumes 100% of the $Br_2$, with the brominated methane distribution being 80% (21.3% yield/pass) $CH_3Br/HBr$, 15% $CH_2Br_2/2HBr$ (4.0%), and 5% $CHBr_3/3HBr$ (1.3%), giving 25.6% overall conversion of methane per pass.

Example D

Catalyst Preparation $Nb_2O_5$ (0.8000 g) was mixed with 0.500 ml 96(w)% $H_2SO_4$, then the mixture was heated at 110° C. for 4 hours. The temperature increased to 500° C. within 6 hours, and kept at 500° C. for 4 hours. Catalyst C1 was obtained.

Testing

Reaction Conditions:

The catalyst was tested at a methane flow of 1.5 ml/minute and Bed flow of 0.07 ml/hour. The reaction temperature was 400° C. The reaction was carried out in a microreactor system. After 6 hours' on line reaction, the reaction effluent was analyzed by a GC/MS. A methane conversion of 24%(mol) with 95% $CH_3Br$ was obtained.

Summarizing the overall process in Reaction 1:

$$CH_4 + Br_2 > HBr + CH_3Br + CH_2Br_2 + CHBr_3 \text{cat} \qquad (1)$$

Reaction 2

Example 1

Reaction on M1

For all examples above the second stage of the process occurs as follows. After separation of the $CH_2Br_2$ and $CHBr_3$ products from the gas stream, the $CH_3Br$, together with the HBr are passed into the next reactor, which contains M1 (50% CuO on $ZrO_2$) and is maintained at 225° C. Flowing the reactant gases at 10 h$^{-1}$ gives a 96% conversion of $CH_3Br+HBr$ to $CH_3OCH_3$ and $H_2O$, or to $CH_3OH$, or a mixture of $CH_3OH$, $CH_3OCH_3$, and $H_2O$, with 93% selectivity, the remaining product being $CuBr_2/ZrO_2$ and 6% $CO_2$. Dimethyl ether and water are converted into methanol if desired in a third reactor containing catalysts.

Example 2

Metal Oxide Preparation

Zr Solution Preparation $Zr(OCH_2CH_2CH_3)_4$ (70(w)% in isopropanol, 112.6 ml) was dissolved into acetic acid (275 ml) under stirring. After stirring for 10 minutes, the solution was diluted by water to make a total volume of 500 ml. A solution with a Zr concentration of 0.5 M was obtained.

Preparation of M2

$Cu(NO_3)_2$ (0.5 M, 7.200 ml) solution was added into $BaBr_2$ (0.5 M, 0.800 ml). A clear solution was obtained. To this solution, Zr solution (0.5 M) as prepared above was added under stirring. After stirring a few seconds, a gel was obtained. The gel was dried at 110° C. for 4 hours, then heated to 500° C. within 6 hours, and kept at 500° C. for 4 hours. M2 was obtained. The metal oxide mixture was tested at a CH$_3$Br flow of 1.0 ml/minute at 230° C. In the first half hour, the average CH$_3$Br conversion is 65%, and the average dimethyl ether selectivity is 90.5%.

Catalyst Preparation (M3)

ZrO$_2$ (2.0000 g) was mixed with H$_2$SO$_4$ (3.000 ml, 96(w)%), then the mixture was heated at 110° C. for 4 hours. The temperature increased to 500° C. within 6 hours, and kept at 500° C. for 4 hours. Catalyst C2 was obtained. Cu(NO$_3$)$_2$ (0.5 M, 40.000 ml) solution was added into Zr solution (0.5 M, 30.000 ml as prepared above). After stirring a few seconds, a gel was obtained. The gel was dried at 110° C. for 4 hours, then heated to 500° C. within 6 hours, and calcined at 500° C. for 4 hours. M3 was obtained.

Testing

The catalyst C2 (2.0000 g) was loaded in the first reactor (R1). After reaction the gas mixture was lead to a trap, which contained 2.0000 g M3. In the trap, HBr was cleared up. After the gas mixture passed through the trap, it was led to the second reactor (R2), which was loaded with M3 (0.8500 g). Reactants methane and bromine were fed into the first reactor (methane flow of 1.5 ml/minute, Br$_2$ flow of 0.07 ml/hour). The reaction temperature was 390° C. After reaction in R1 (stabilized by online reaction for more than 8 hours) and passed through the trap, a mixture of methane and CH$_3$Br (containing 20% mol of CH$_3$Br) was obtained. This gas mixture was directly fed into R2 at 220° C. In the first one hour, an average CH$_3$Br conversion of 91% with an average dimethyl ether selectivity of 75% was obtained.

Summarizing the overall process in Reaction 2:

$$CH_3Br + HBr + CuO > CH_3OH + CuBr_2 \qquad (2)$$

Possible variations of Reaction 2:

$$2\, HBr + CuO > H_2O + CuBr_2 \qquad (2a)$$

$$2\, CH_3Br + CuO > CH_3OCH_3 + CuBr_2 \qquad (2b)$$

Reaction 3

The solid CuBr$_2$/ZrO$_2$ is transferred from Reactor 2 to Reactor 3 and is simply treated with O$_2$ at 300° C. to yield Br$_2$ and CuO/ZrO$_2$ in 100% yield and conversion. This reaction may be run at 100 h$^{-1}$.

Summarizing the overall process in Reaction 3:

$$CuBr_2/ZrO_2 + \tfrac{1}{2}O_2 > Br_2 + CuO/ZrO_2 \qquad (3)$$

Overall $$CH_4 + \tfrac{1}{2}O_2 > CH_3OH \qquad (A)$$

Possible variation:

$$CH_4 + \tfrac{1}{2}O_2 > \tfrac{1}{2}CH_3OCH_3 + \tfrac{1}{2}H_2O \qquad (B)$$

It will therefore be understood that the method and apparatus of the present invention operates on a continuous or batch basis to convert alkanes to alcohols and ethers. The method and apparatus of the present invention operates at relatively low temperatures and at low pressures and is therefore economical to manufacture and use. The bromine, which is utilized in the method and apparatus of the present invention, is continuously recycled. The metal oxide catalyst which is utilized in the process is continuously refreshed.

Although preferred embodiments of the invention have been illustrated in the accompanying Drawings and described in the foregoing Detailed Description, it will be understood that the invention is not limited to the embodiments disclosed but is capable of numerous rearrangements, modifications, and substitutions of parts and elements without departing from the spirit of the invention.

What is claimed is:

1. A method for synthesizing alcohols and/or ethers from alkanes comprising:

providing a quantity of an alkane selected from the group consisting of methane, ethane, propane, butane, and isobutane;

providing a quantity of bromine;

mixing the alkane and the bromine and thereby forming an alkyl bromide and hydrogen bromide;

reacting the alkyl bromide and the hydrogen bromide with a metal oxide and thereby forming alcohol and/or ether and a metal bromide;

oxidizing the metal bromide to form the original metal oxide and bromine;

recycling the metal oxide; and recycling the bromine.

2. The method according to claim 1 wherein the step of mixing the alkane and the bromine is carried out at a high alkane to bromine concentration.

3. The method according to claim 1 wherein the step of mixing the alkane and the bromine is carried out at a temperature of between about 20° C. and about 400° C.

4. The process according to claim 1 wherein the step of reacting the alkane with the bromine to form the alkyl bromide and hydrogen bromide and the step of contacting the alkyl bromide with metal oxides are carried out continuously.

5. The process according to claim 1 wherein the step of reacting the alkane with the bromine to form the alkyl bromide and hydrogen bromide and the step of contacting the alkyl bromide and the hydrogen bromide with metal oxides are carried out in a batch reaction.

6. The method according to claim 1 wherein the step of oxidizing the metal bromide to form the original metal oxide and bromine, the step of re cycling the metal oxide, and the step of recycling the bromine are carried out continuously.

7. The method according to claim 1 wherein the step of oxidizing the metal bromide to form the original metal oxide and bromine, the step of recycling the metal oxide, and the step of recycling the bromine are carried out in a batch reaction.

8. A method for converting methane to methanol comprising:

providing a quantity of methane;

providing a quantity of bromine;

reacting the methane with the bromine and thereby forming methyl bromide and hydrogen bromide;

reacting the methyl bromide and the hydrogen bromide catalyst with a metal oxide catalyst and thereby forming methanol and a metal bromide;

oxidizing the metal bromide to form the original metal oxide and bromine;

recycling the metal oxide; and recycling the bromine.

9. The method according to claim 8 wherein the step of mixing the methane and the bromine is carried out at a methane to bromine ratio from about 1:10 to about 100:1 (by mole).

10. The method according to claim 8 wherein the step of mixing the methane and the bromine is carried out at a methane to bromine ratio from about 1:1 to about 10:1 (by mole).

11. The process according to claim 8 wherein the step of mixing the methane and the bromine is carried out at a methane to bromine ratio from about 1:1 to about 5:1 (by mole).

12. The method according to claim 8 wherein the step of mixing the methane and the bromine is carried out at a temperature of between about 20° C. and about 400° C.

13. The process according to claim 8 wherein the step of mixing the methane and the bromine to form the methyl bromide and hydrogen bromide and the step of contacting the methyl bromide and the hydrogen bromide with a metal oxide are carried out continuously.

14. The process according to claim 8 wherein the step of mixing the methane and the bromine to form the methyl bromide and hydrogen bromide and the step of contacting the methyl bromide and the hydrogen bromide with a metal oxide are carried out in a batch reaction.

15. The method according to claim 8 wherein the step of oxidizing the metal bromide to form the original metal oxide catalyst and bromine, the step of recycling the metal oxide, and the step of recycling the bromine are carried out continuously.

16. The method according to claim 8 wherein the step of oxidizing the metal bromide to form the original metal oxide and bromine, the step of recycling the metal oxide, and the step of recycling the bromine are carried out in a batch reaction.

17. A method for synthesizing ethers from alkanes comprising:
providing a quantity of an alkane selected from the group consisting of methane and ethane;
providing a quantity of bromine;
mixing the alkane and the bromine and thereby forming an alkyl bromide and hydrogen bromide;
reacting the alkyl bromide with a metal oxide and thereby forming an ether and a metal bromide;
oxidizing the metal bromide to form the original metal oxide catalyst and bromine;
recycling the metal oxide catalyst; and
recycling the bromine.

18. The method according to claim 17 wherein the step of mixing the alkane and the bromine is carried out at a alkane to bromine mol ratio between about 1:2 to about 100:1.

19. The method according to claim 17 wherein the step of mixing the alkane and the bromine is carried out at a alkane to bromine mol ratio between about 1:1 to about 50:1.

20. The method according to claim 17 wherein the step of mixing the alkane and the bromine is carried out at a alkane to bromine mol ratio between about 2:1 to about 10:1.

21. The method according to claim 17 wherein the step of mixing the alkane and the bromine is carried out at a temperature of between about 20° C. and about 400° C.

22. The process according to claim 17 wherein the step of mixing the alkane and the bromine to form the alkyl bromide and hydrogen bromide and the step of contacting the alkyl bromide and the hydrogen bromide with a metal oxide are carried out continuously.

23. The process according to claim 17 wherein the step of mixing the alkane and the bromine to form the alkyl bromide and hydrogen bromide and the step of contacting the alkyl bromide and the hydrogen bromide with a metal oxide are carried out in a batch reaction.

24. The method according to claim 17 wherein the step of oxidizing the metal bromide to form the original metal oxide and bromine, the step of recycling the metal oxide catalyst, and the step of recycling the bromine are carried out continuously.

25. The method according to claim 17 wherein the step of oxidizing the metal bromide to form the original metal oxide and bromine, the step of recycling the metal oxide, and the step of recycling the bromine are carried out in batch reactions.

26. A method for converting methane to dimethyl ether comprising:
providing a quantity of methane;
providing a quantity of bromine;
mixing the methane and the bromine and thereby forming methyl bromide and hydrogen bromide;
trapping the HBr by metal oxide;
reacting the methyl bromide with a metal oxide and thereby forming dimethyl ether and a metal bromide;
oxidizing the metal bromide to form the original metal oxide and bromine;
recycling the metal oxide; and
recycling the bromine.

27. The method according to claim 26 wherein the step of mixing the methane and the bromine is carried out at a methane to bromine mol ratio between about 1:2 to about 100:1.

28. The method according to claim 26 wherein the step of mixing the methane and the bromine is carried out at a methane to bromine mol ratio between about 1:1 to about 50:1.

29. The method according to claim 26 wherein the step of mixing the methane and the bromine is carried out at a methane to bromine mol ratio between about 2:1 to about 10:1.

30. The method according to claim 26 wherein the step of mixing the methane and the bromine is carried out at a temperature of between about 20° C. and about 400° C.

31. The process according to claim 26 wherein the step of mixing the methane and the bromine to form the methyl bromide and hydrogen bromide, the step of trapping HBr by metal oxide, and the step of contacting the methyl bromide with metal oxides is carried out continuously.

32. The method according to claim 26 wherein the step of oxidizing the metal bromide to form the original metal oxide and bromine, the step of recycling the metal oxide, and the step of re cycling the bromine are carried out continuously.

* * * * *